United States Patent
Kim

(10) Patent No.: US 9,987,220 B2
(45) Date of Patent: Jun. 5, 2018

(54) PAD FOR HERBAL MEDICINE IN WHICH RELEASE OF MEDICINAL INGREDIENT CAN BE CONTROLLED, AND MANUFACTURING METHOD THEREOF

(75) Inventor: Hi Gu Kim, Gwangju (KR)

(73) Assignees: BM BIOTECHNOLOGY CO., LTD., Gyeongsangnam-Do (KR); Hi Gu Kim, Gwangju (KR)

( * ) Notice: Subject to any disclaimer, the term of this patent is extended or adjusted under 35 U.S.C. 154(b) by 918 days.

(21) Appl. No.: 13/395,347

(22) PCT Filed: Sep. 14, 2010

(86) PCT No.: PCT/KR2010/006250
§ 371 (c)(1),
(2), (4) Date: May 7, 2012

(87) PCT Pub. No.: WO2011/031116
PCT Pub. Date: Mar. 17, 2011

(65) Prior Publication Data
US 2012/0209056 A1    Aug. 16, 2012

(30) Foreign Application Priority Data

Sep. 14, 2009  (KR) .................. 10-2009-0086728

(51) Int. Cl.
| | | |
|---|---|---|
| A61M 37/00 | (2006.01) | |
| A61K 9/70 | (2006.01) | |
| A61K 9/00 | (2006.01) | |

(52) U.S. Cl.
CPC .......... *A61K 9/0014* (2013.01); *A61K 9/7007* (2013.01)

(58) Field of Classification Search
CPC ............................ A61K 9/7007; A61K 9/0014
See application file for complete search history.

(56) References Cited

U.S. PATENT DOCUMENTS

| | | | | |
|---|---|---|---|---|
| 2002/0147424 | A1* | 10/2002 | Ostrow et al. .................. 604/20 |
| 2007/0020320 | A1* | 1/2007 | David et al. .................. 424/445 |
| 2007/0254044 | A1* | 11/2007 | Karandikar et al. .......... 424/618 |
| 2008/0131493 | A1* | 6/2008 | Matloub ........................ 424/449 |
| 2009/0011051 | A1* | 1/2009 | Roth ..................... A01N 1/0205 |
| | | | | 424/699 |
| 2014/0161842 | A1* | 6/2014 | Lin ........................ A61L 27/54 |
| | | | | 424/400 |

FOREIGN PATENT DOCUMENTS

| | | | |
|---|---|---|---|
| CN | 1056419 | * | 11/1991 |
| KR | 1998-066346 | | 10/1998 |
| KR | 10-2002-0003462 A | | 1/2002 |
| KR | 10-2002-0021314 A | | 3/2002 |
| KR | 10-2005-0116503 A | | 12/2005 |
| WO | WO 2004/110428 A1 | | 12/2004 |
| WO | WO 2005/013943 A1 | | 2/2005 |

OTHER PUBLICATIONS

English Machine Translation of CN 1056419; published: Nov. 27, 1991; obtained on Apr. 4, 2016.*
International Search Report from International Application No. PCT/KR2010/006250, dated Jun. 3, 2011.

* cited by examiner

*Primary Examiner* — Johann R Richter
*Assistant Examiner* — Genevieve S Alley
(74) *Attorney, Agent, or Firm* — Womble Bond Dickinson (US) LLP

(57) ABSTRACT

A method for manufacturing a pad for herbal medicine in which the release of medicinal ingredients can be controlled, which comprises: separating two or more medicinal herbal ingredients prescribed or prepared according to pharmacological effects on the basis of the weight ratio of each medicinal ingredient to total weight of the medicinal ingredients; grinding the medicinal ingredients separated on the basis of weight ratio, wherein fine particles are ground to different sizes according to the setting of release duration; preparing herbal medicine by mixing the ground medicinal ingredients together, and then mixing the ingredients with a binding agent; and adhering the herbal medicine to a base sheet. The pad for herbal medicine manufactured according to the method allows for persistent permeation of medical ingredients through the skin with different release rate for each medicinal ingredient, thus maximizing the efficacy of the medicinal ingredient layer and the effect of treating disease.

10 Claims, 2 Drawing Sheets

【Fig. 1】
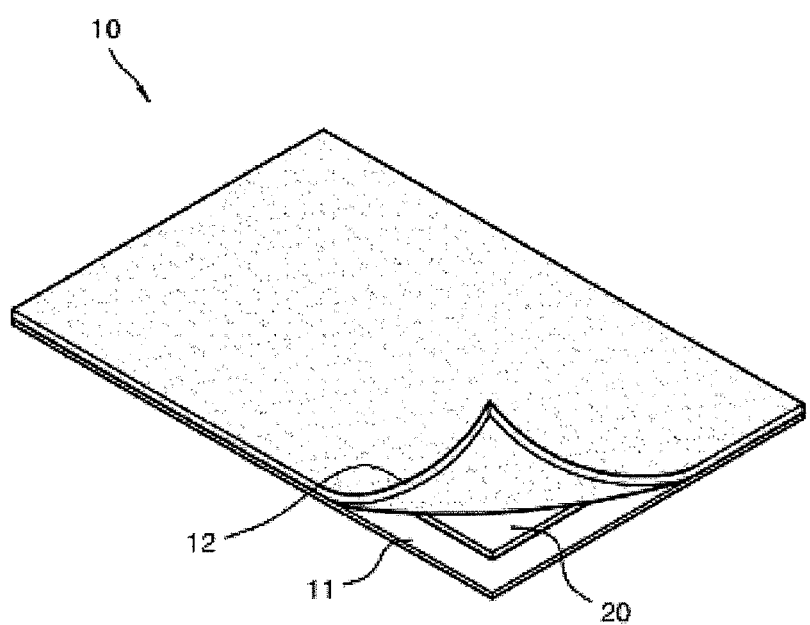

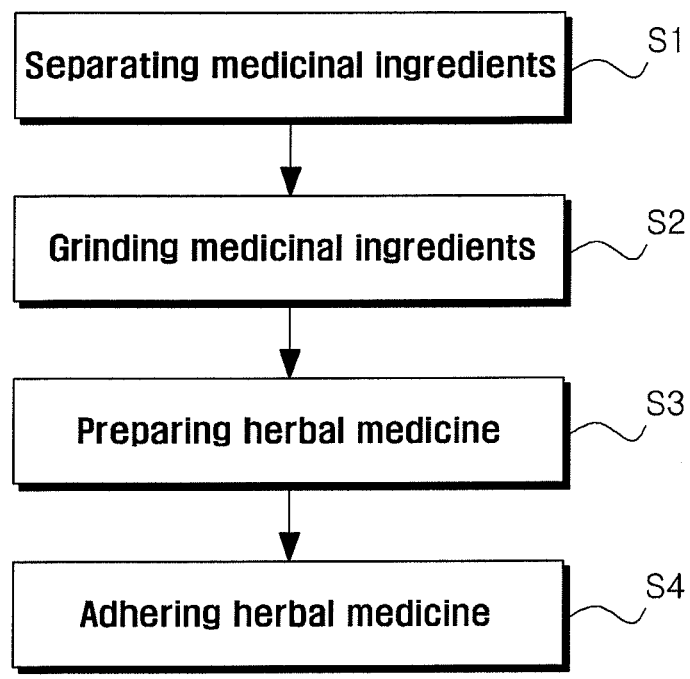

PAD FOR HERBAL MEDICINE IN WHICH RELEASE OF MEDICINAL INGREDIENT CAN BE CONTROLLED, AND MANUFACTURING METHOD THEREOF

CROSS-REFERENCE TO RELATED APPLICATION

This application is a national stage application filed under 35 U.S.C. 371 of International Application No. PCT/KR2010/006250, filed Sep. 14, 2010, which claims priority from Korean Application No. 10-2009-0086728, filed Sep. 14, 2009, each of which is incorporated by reference herein in its entirety.

TECHNICAL FIELD

The present disclosure relates to a pad for herbal medicine and a method for manufacturing the same. More particularly, it relates to a pad for herbal medicine allowing for persistent supply of medical ingredients through skin or respiratory organs and a method for manufacturing the same.

BACKGROUND ART

In general, drug delivery through the skin is achieved by electrophoresis or electroosmosis. The drug administered transdermally in this manner reaches the bloodstream, being aided by ions. In particular, in case of electroosmosis, aqueous solution is attracted to the negative (−) electrode and current flows via membrane with small pores.

Drug administration using devices related to these techniques is quite limited. U.S. Pat. Nos. 2,493,155, 4,141,359, 4,250,878, 3,163,166, 4,166,457, 4,273,135, 3,289,671, 4,239,052, 4,367,745, 3,677,268 and 4,243,052 disclose methods for administering drugs through skin.

Particularly, it is to be noted that, according to U.S. Pat. Nos. 3,289,671 and 4,141,359, the rate of drug administration is a function of current and the control of current is critical in controlling the amount of drug administration. U.S. Pat. No. 588,479 discloses an electric herb pad providing electrical effect as well as herbal medicinal effect at the same time for human body.

Iontophoresis is a transdermal drug administration technique capable of complementing or replacing existing oral administration or injection. Differently from the passive drug transport using a pad attached to the skin, it enables active transport of soluble drug through the skin using electric induction. In an iontophoretic apparatus, a drug pad containing drug is attached to the skin. Then magnetic or electrical stimulation is applied to the drug pad such that the drug pad is maintained in a positively or negatively charged state and the drug is penetrated into the skin owing to electrical or magnetic repulsion. The iontophoretic technique is used in cooling or heating pads for drug delivery.

Korean Patent No. 0775675 discloses a vibration pad to stimulate the body for physiotherapy and an apparatus for controlling the same.

The pad is configured such that the drug ingredient is easily absorbed into the skin by applying electric field or magnetic field to a medicinal ingredient layer formed in the pad.

However, the patent focuses only on the fast penetration of drug without considering the persistence of the drug administration through the skin and, thus, it is difficult to persistently administer the drug through the skin. Moreover, it is impossible to vary the rate of penetration depending on the particular drug included in the medicinal ingredient layer.

When preparing herbal medicine from plants by mixing different ingredients obtained from, for example, the whole plant, leaves, root and rhizome, fruit and seed, flower, bark, stem, or the like, it may be necessary to control the time or amount of penetration into the skin according to pharmacological effect so as to achieve persistent drug delivery, which is difficult to be achieved with existing pads or patches.

DISCLOSURE

Technical Problem

The present disclosure is directed to solving the above-described problems and providing a pad for herbal medicine in which the release and penetration of medicinal ingredients to the skin can be controlled differently for different medical ingredients so as to maximize the therapeutic effect and a method for manufacturing the same.

The present disclosure is also directed to providing a pad for herbal medicine in which the release of medicinal ingredients can be controlled by applying electrical stimulation or magnetic force to the pad to improve the efficiency of penetration into the skin and a method for manufacturing the same.

The present disclosure is also directed to providing a pad for herbal medicine in which the release of medicinal ingredients can be controlled allowing for maintenance of physical properties of two or more herbal medicinal ingredients prescribed according to pharmacological effects, long-term storage of the ground herbal medicinal ingredients at room temperature, control of release amount and release duration of the medicinal ingredients and maximized delivery effect of the medical ingredients via skin or respiratory organs, and a method for manufacturing the same.

Technical Solution

In one general aspect, the present disclosure provides a method for manufacturing a pad for herbal medicine in which the release of medicinal ingredients can be controlled, which comprises:

separating two or more medicinal ingredients prescribed or prepared according to pharmacological effects on the basis of the release duration of the medicinal ingredients;

grinding the separated medicinal ingredients to fine particles with different sizes on the basis of the release duration of the medicinal ingredients;

preparing herbal medicine by mixing the ground medicinal ingredients with a binding agent; and adhering the prepared herbal medicine to a base sheet.

In an exemplary embodiment of the present disclosure, the binding agent may be maltodextrin or natural polymer.

In the step of preparing the herbal medicine, a step of providing a medicinal ingredient permeation activating unit of providing a magnet or a low frequency generator for applying magnetic field or low frequency to the medicinal ingredients of the pad may be further included.

In another general aspect, the present disclosure provides a pad for herbal medicine comprising:

a base sheet; and a medicinal ingredient layer adhered to the base sheet, in which two or more medicinal ingredients prescribed or prepared according to pharmacological effects on the basis of the release duration of the medicinal ingredients which are ground to fine particles of different sizes according to the setting of release duration are mixed with a binding agent comprising maltodextrin or natural polymer.

The pad may further comprise a medicinal ingredient permeation activating unit provided on base sheet or between the medicinal ingredient layer and the base sheet, and the medicinal ingredient permeation activating unit may comprise a magnet or a low frequency generator.

Advantageous Effects

The pad for herbal medicine and the method for manufacturing the same according to the present disclosure allow for persistent permeation of medical ingredients through the skin with different release rate for each medicinal ingredient, and thus, the efficacy of the medicinal ingredient layer and the effect of treating disease can be maximized.

Since the pad according to the present disclosure can be manufactured as a mask, necklace, bracelet, or the like, for penetration of medicinal ingredients into the skin, treatment may be achieved more conveniently and the commercial value may be enhanced.

In addition, the pad for herbal medicine of the present disclosure may be attached to a mask, necklace, bracelet, compression pad, etc. for treatment purposes so as to deliver prescribed herbal medicinal ingredients. Since the pad for herbal medicine can deliver medicinal ingredient through the skin, it may be developed into various products.

DESCRIPTION OF DRAWINGS

FIG. 1 is a schematic perspective view of a pad for herbal medicine according to the present disclosure.

FIG. 2 is a block diagram illustrating a method for manufacturing a pad for herbal medicine according to the present disclosure.

BEST MODE

A pad for herbal medicine according to the present disclosure allows medicinal ingredients to penetrate into the skin with controlled penetration time, i.e. release duration, for treatment of diseases. An exemplary embodiment is shown in FIG. 1.

Referring to the figure, a pad 10 according to the present disclosure comprises a base sheet 11 comprising non-woven cloth, a medicinal ingredient layer 12 having a predetermined thickness and spread to the base sheet 11, and a medicinal ingredient permeation activating unit 20 provided on base sheet 11 or between the medicinal ingredient layer 12 and the base sheet 11, the medicinal ingredient permeation activating unit 20 comprising a magnet or a low frequency generator for applying magnetic field or low frequency.

The base sheet 11 may comprise non-woven cloth, but is not limited thereto. For example, the base sheet may comprise synthetic resin, natural fiber, paper, natural nonwoven, or the like. In particular, the base sheet 11 may be further provided with a magnet powder layer as a medicinal ingredient permeation activating unit.

The medicinal ingredient layer 12 comprises two or more medicinal ingredients prescribed or prepared according to pharmacological effects on the basis of the release duration of the medicinal ingredients which are ground to fine particles of different sizes according to the setting of penetration time, i.e. release duration, and mixed (or encapsulated) with a binding agent. When a relatively long release duration is desired, the medical ingredient may be ground to relatively large particle size (10-400 μm), and, when a relatively short release duration is desired, the medical ingredient may be ground to have a particle size of 10-15 μm. For example, when the medical ingredient is desired to be released for a duration of from 1 day to 1 year or longer, the medical ingredient may be ground to have a particle size of from 10 μm up to 400 μm. And, when two or more medical ingredients are desired to be released persistently until the release of all the medical ingredients is completed, the medical ingredients may be ground to fine particles of different sizes from 10 μm up to 400 μm based on their relative weight, so that the medical ingredient of small amount has a larger size and that with a large amount has a smaller size.

Specifically, the binding agent which encapsulates the ground medical ingredient may comprise maltodextrin or natural polymer which is capable of preventing decomposition of the medical ingredient for a long period of time and holding moisture. The binding agent may be used in an amount of not greater than 40% (40/100) of the total weight of the ground herbal medicine. When the binding agent is mixed with the ground herbal medicine, the mixing speed may be 100 rpm or lower. And, when honey, which is a natural polymer, is used as the binding agent, the amount may be not greater than 80-90 parts by weight based on 100 parts by weight of the ground herbal medicine, considering the water-holding ability of honey.

The medicinal ingredient permeation activating unit 20 is capable of activating the permeation of the medicinal ingredient into the skin by applying electric field or magnetic field to the medicinal ingredient layer. A magnetic substance capable of applying a magnetic force of 2500-7000 gauss may be provided between the medicinal ingredient layer 12 and the base sheet 11. The magnetic substance may comprise a rubber magnet, and may be provided as the magnet powder layer of the base sheet as described above or may be embedded or mixed as magnet powder in the base sheet.

In another exemplary embodiment, the medicinal ingredient permeation activating unit may comprise a low frequency generator (not shown) provided on one side of the base sheet and a low frequency transport layer connected to the low frequency generator and embedded in the medicinal ingredient layer. Without being limited to the above-described embodiments, the medicinal ingredient permeation activating unit may be of any configuration capable of activating the penetration of the medicinal ingredient into the skin. For example, a light-emitting diode radiating light of specific wavelength region to the target site may be used.

In addition, an auxiliary sheet having a number of holes may be attached on the medicinal ingredient layer. Also, a protection sheet for protecting the medicinal ingredient layer until use may be further provided.

The pad for herbal medicine may be used after being attached to a mask, necklace, bracelet, compression pad, or the like. When it is attached to a bracelet, compression pad or necklace, the pad for herbal medicine may be disposed such that it contacts with the skin.

The pad for herbal medicine comprising two or more medicinal ingredients prescribed or prepared according to pharmacological effects may be modified to suit the site of application and be attached thereto so as to achieve controlled release duration of the medical ingredient according to purposes such as treatment of neuralgia, arthritis, shoulder stiffness, etc.

The particle size of the two or more medicinal ingredients may be determined by the following equation. The equation is based on the physical principle that the smaller the particle size the shorter is the release duration, and the larger the particle size the longer is the release duration.

$$\log \frac{S}{S_o} = \frac{2\gamma V}{2.303RTr}$$

S: release amount of relatively small-sized particles, $S_o$: release amount of relatively large-sized particles, γ: surface tension of particles, V: molecular volume (cm$^3$), r: final diameter (cm) of particles, R: gas constant (8.314×10$^7$ erg/deg mol), T: absolute temperature.

A method for manufacturing the pad for herbal medicine comprises, as shown in FIG. 2, separating two or more medicinal ingredients prescribed or prepared according to pharmacological effects on the basis of the release duration of the medicinal ingredients into the skin (S1) and grinding the separated medicinal ingredients to fine particles with different sizes on the basis of the release duration of the medicinal ingredients (S2). The particle size of the finely ground medicinal ingredients may be determined according to the weight proportion of the medicinal ingredients. Specifically, a medicinal ingredient with a smaller weight proportion may be ground to have a relatively larger particle size.

The method for manufacturing the pad for herbal medicine further comprises preparing herbal medicine by mixing the ground medicinal ingredients with a binding agent (S3) and adhering the prepared herbal medicine to a base sheet (S4). The step of preparing the herbal medicine may comprise mixing the ground medicinal ingredients with a binding agent comprising honey, maltodextrin or natural polymer such that the medicinal ingredients are encapsulated by the binding agent. In the adhering step, the herbal medicine is coated on the base sheet. It may further comprise providing a medicinal ingredient permeation activating unit comprising a magnet or a low frequency generator for applying magnetic field or low frequency to the medicinal ingredients of the pad.

The present disclosure is described in more detail by the following test examples. However, the scope of present disclosure is not limited by the test examples.

Test Example 1

Release duration of medicinal ingredients prescribed for skin disease and inflammation having different particle sizes was tested. Herbal medicine was prepared from red bean (3 g), apricot kernel (4 g), ephedra, forsythia, ginger, jujube and mulberry root (3 g each) and licorice (1 g).

The apricot kernel was ground to a particle size of 10 μm (minimum particle size required for maintaining the physical properties of the herbal medicine), the red bean, ephedra, forsythia, jujube and mulberry root were ground to a particle size of 15 μm, and the licorice was ground to a particle size of 40 μm.

The ground medicinal ingredients were mixed with 80 parts by weight of honey based on the total weight of the ground medicinal ingredients and applied on a base sheet to form a 5 mm thick medicinal ingredient layer.

Thus prepared pad for herbal medicine was cut to a sample of 50 mm×50 mm size and adhered to the disease site. Then, the rate and time of release of the medicinal ingredients from the medicinal ingredient layer were measured. The drug release amount was measured by atomic analysis of the medical ingredients after a given period of time.

The release amount from the medicinal ingredient layer was measured 24 hours after attaching the pad on the knee. At 24 hours, the release amount was 45% and 40% of initial release for red bean and apricot kernel, respectively. The release amount of ephedra, forsythia, jujube and mulberry root was 45% of initial release. And, the release amount of licorice with a relatively larger particle size was 40% of initial release. As seen from Table 1, the time and amount of release of the medicinal ingredients are determined by the particle size, without regard to the content of the medicinal ingredients.

TABLE 1

|  | Weight (g) of medicinal ingredient | Particle size (μm) | Release ratio (%) | Note |
| --- | --- | --- | --- | --- |
| Licorice | 1 | 40 | 40 |  |
| Red bean | 3 | 15 | 45 |  |
| Ephedra | 3 | 15 | 45 |  |
| Forsythia | 3 | 15 | 45 |  |
| Jujube | 3 | 15 | 45 |  |
| Mulberry root | 3 | 15 | 45 |  |
| Ginger | 3 | 15 | 45 |  |
| Apricot kernel | 4 | 10 | 40 |  |

Test Example 2

Herbal medicine was prepared as in Test Example 1. The red bean, apricot kernel, ephedra, forsythia, jujube and mulberry root were ground to a particle size of 20 μm, and the licorice was ground to a particle size of 25 μm.

The ground medicinal ingredients were mixed with 90 parts by weight of honey based on the total weight of the ground medicinal ingredients and applied on a base sheet to form a 5-mm thick medicinal ingredient layer.

The release from the medicinal ingredient layer was determined 7 days after attaching the pad on the knee. The release amount of red bean was 10% of initial release, and the release amount of ephedra, forsythia, jujube and mulberry root was 10.3% of initial release. The release amount of licorice with a relatively larger particle size was 20% of initial release.

Test Example 3

Herbal medicine was prepared as in Test Example 1. The red bean was ground to a particle size of 370 μm, the apricot kernel, ephedra, forsythia, jujube and mulberry root were ground to a particle size of 375 μm, and the licorice was ground to a particle size of 300 μm.

The release from the medicinal ingredient layer was determined 7 days after attaching the pad on the knee. The release amount of red bean was 11% of initial release, and the release amount of ephedra, forsythia, jujube and mulberry root was 11.2% of initial release. The release amount of licorice with a relatively larger particle size was 5% of initial release.

Test Example 4

Experiment was performed under the same condition as in Test Example 1 after attaching a magnet of 2,600 gauss to the base sheet.

The release from the medicinal ingredient layer was determined 24 hours after attaching the pad on the knee. The release amount of red bean was 3% of initial release, and the release amount of ephedra, forsythia, jujube and mulberry root was 3.5% of initial release. The release amount of licorice with a relatively larger particle size was 3% of initial release.

Those skilled in the art will appreciate that the conceptions and specific embodiments disclosed in the foregoing description may be readily utilized as a basis for modifying or designing other embodiments for carrying out the same purposes of the present disclosure.

Those skilled in the art will also appreciate that such equivalent embodiments do not depart from the spirit and scope of the disclosure as set forth in the appended claims.

The invention claimed is:

1. A method for manufacturing a pad for herbal medicine suitable for respiratory administration in which the release of medicinal ingredients of the herbal medicine to respiratory organs can be controlled, which comprises:
   separating two or more medicinal ingredients of the herbal medicine prescribed or prepared according to pharmacological effects on the basis of the release duration of the medicinal ingredients of the herbal medicine via the respiratory organs, wherein the separated medicinal ingredients comprise a first ingredient and a second ingredient;
   grinding the separated medicinal ingredients to fine particles with different sizes on the basis of the release duration of the medicinal ingredients, wherein the first ingredient defines a first particle size and the second ingredient defines a second particle size, wherein the first particle size is larger than the second particle size, such that the second ingredient is configured to release at a greater rate than the first ingredient, and wherein a first weight of the first medicinal ingredient is less than a second weight of the second ingredient;
   preparing herbal medicine by mixing the ground medicinal ingredients with a binding agent comprising maltodextrin or natural polymer, wherein the first ingredient and the second ingredient define a same release duration, such that the first ingredient and the second ingredient are configured to be released persistently until the release of all the medicinal ingredients is completed;
   adhering the herbal medicine to a base sheet; and disposing an auxiliary sheet having a number of holes on a surface of the base sheet, onto which the herbal medicine is adhered, or disposing a protection sheet on a surface of the base sheet, onto which the herbal medicine is adhered.

2. The method for manufacturing a pad for herbal medicine in which the release of medicinal ingredients can be controlled of claim 1, wherein said preparing the herbal medicine further comprises providing a medicinal ingredient permeation activating unit comprising a magnet or a low frequency generator for applying magnetic field or low frequency to the medicinal ingredients of the pad.

3. The method for manufacturing a pad for herbal medicine in which the release of medicinal ingredients can be controlled of claim 2, wherein the medicinal ingredient permeation activating unit comprises a magnet powder layer of the base sheet.

4. The method for manufacturing a pad for herbal medicine in which the release of medicinal ingredients can be controlled of claim 3, wherein the magnet powder layer comprises a rubber magnet.

5. The method for manufacturing a pad for herbal medicine in which the release of medicinal ingredients can be controlled of claim 2, further comprising a medicinal ingredient layer comprising the herbal medicine, wherein the medicinal ingredient permeation activating unit is positioned between the medicinal ingredient layer and the base layer.

6. The method for manufacturing a pad for herbal medicine in which the release of medicinal ingredients can be controlled of claim 5, wherein the medicinal ingredient permeation activating unit comprises a rubber magnet.

7. The method for manufacturing a pad for herbal medicine in which the release of medicinal ingredients can be controlled of claim 1, wherein the binding agent comprises 40% or less of a total weight of the ground medicinal ingredients.

8. The method for manufacturing a pad for herbal medicine in which the release of medicinal ingredients can be controlled of claim 1, wherein the binding agent comprises honey.

9. The method for manufacturing a pad for herbal medicine in which the release of medicinal ingredients can be controlled of claim 1, wherein at least one of the first particle size of the first ingredient or the second particle size of the second ingredient is from 10 µm to 400 µm.

10. The method for manufacturing a pad for herbal medicine in which the release of medicinal ingredients can be controlled of claim 1, wherein the first particle size of the first ingredient and the second particle size of the second ingredient are from 10 µm to 400 µm.

* * * * *